United States Patent
Coomber

(10) Patent No.: US 10,517,981 B2
(45) Date of Patent: Dec. 31, 2019

(54) WOUND DRESSING MATERIALS INCORPORATING ANTHOCYANINS DERIVED FROM FRUIT OR VEGETABLE SOURCES

(71) Applicant: Allison Coomber, Auburn, MA (US)

(72) Inventor: Allison Coomber, Auburn, MA (US)

(*) Notice: Subject to any disclaimer, the term of this patent is extended or adjusted under 35 U.S.C. 154(b) by 198 days.

(21) Appl. No.: 15/830,188

(22) Filed: Dec. 4, 2017

(65) Prior Publication Data

US 2018/0093007 A1   Apr. 5, 2018

Related U.S. Application Data

(62) Division of application No. 14/514,579, filed on Oct. 15, 2014, now Pat. No. 9,855,364.

(51) Int. Cl.
| | | |
|---|---|---|
| *A61K 49/00* | (2006.01) | |
| *A61L 15/56* | (2006.01) | |
| *A61L 15/40* | (2006.01) | |
| *A61L 15/44* | (2006.01) | |

(52) U.S. Cl.
CPC .......... *A61L 15/40* (2013.01); *A61K 49/0004* (2013.01); *A61K 49/006* (2013.01); *A61L 15/44* (2013.01); *A61L 15/56* (2013.01)

(58) Field of Classification Search
None
See application file for complete search history.

(56) References Cited

U.S. PATENT DOCUMENTS

| | | |
|---|---|---|
| 7,183,455 B2 | 2/2007 | Utsugi |
| 7,485,158 B2 | 2/2009 | Baid |
| 2002/0015726 A1 | 2/2002 | Scamilla Aledo et al. |
| 2006/0094996 A1 | 5/2006 | Leber |
| 2007/0003502 A1 | 1/2007 | Tanabe et al. |
| 2007/0101514 A1 | 5/2007 | Kaneko |
| 2007/0248700 A1 | 10/2007 | Alberte et al. |
| 2009/0176718 A1 | 7/2009 | Ribnicky et al. |
| 2012/0301406 A1 | 11/2012 | Yang et al. |
| 2013/0046264 A1 | 2/2013 | Salim |

OTHER PUBLICATIONS

Coomber, "The Effect of pH on Bandages Dyed with a Halochromic Pigment," [student paper] Massachusetts Academy of Math and Science, The Scientia Review [online] retrieved on Feb. 27, 2015; http://www.scientiareview.org/pdfs/406.pdf, 18 pages.

Marszalet et al.; "The Effect of High Pressure Techniques on the Stability of Anthocyanins in Fruit and Begetables"; International Journal of Molecular Sciences; Jan. 27, 2017; 23 pages.

Mongkholrattanasit et al.; "Dyeing Studies with Eucalyptus, Quercetin, Rutin, and Tannin: A Research on Effect of Ferrous Sulfate Mordant"; Journal of Textiles; vol. 2013, Article ID 423842; 2013; 8 pages.

*Primary Examiner* — David J Blanchard
*Assistant Examiner* — John P Nguyen
(74) *Attorney, Agent, or Firm* — Fish & Richardson P.C.

(57) ABSTRACT

A wound dressing composition, such as gauze, bandages, and surgical tapes comprising a substrate material impregnated with a pH sensitive dye composition comprising at least one anthocyanin derived from fruit or vegetable sources, and methods of use thereof.

15 Claims, 4 Drawing Sheets
(2 of 4 Drawing Sheet(s) Filed in Color)

WOUND DRESSING MATERIALS INCORPORATING ANTHOCYANINS DERIVED FROM FRUIT OR VEGETABLE SOURCES

CLAIM OF PRIORITY

This application is a divisional application of U.S. patent application Ser. No. 14/514,579, filed on Oct. 15, 2014, the entire contents of which is hereby incorporated by reference.

TECHNICAL FIELD

The invention generally relates to wound dressings and their methods of use. More particularly, the invention relates to wound dressings dyed with a pH sensitive dye composition comprising at least one anthocyanin obtained from (e.g., derived from) a fruit or vegetable extract, and methods of using the wound dressings for monitoring wound health.

BACKGROUND

The pH of a wound often signifies important information about wound health. Measuring the pH of a wound can provide information about the stage of healing and the presence of infection. The pH of wound leakage has been shown to change as the wound heals and if the wound becomes infected. The natural pH of skin is slightly acidic, ranging from 4.8 to 6.0, an adaptation which wards off bacteria on the surface, but the interstitial fluid in the body has a pH closer to neutral (Romanelli, M, et al., 2002). In healing wounds, pH starts slightly basic, moves to neutral, and then approaches the pH of normal skin (Gethin, G 2007). Healthy wounds usually follow this trend, and it can be problematic if a wound does not. If healing is not progressing, the pH will stay basic. Wounds that remain basic usually heal more slowly because the tissue does not have enough access to oxygen. Small pH changes within a wound can cause large changes in oxygen availability (Leveen, H. et al., 1973). The more oxygen available in a wound, the faster a wound will heal. This makes pH fluctuations critical to wound health and the healing process.

Infection inhibits wound healing by raising wound pH. Many bacteria produce ammonia, which has a pH of 11.6 in a 1.0 M aqueous solution. Ammonia production raises the pH of a wound and lowers the oxygen availability. With a decreased oxygen supply, a wound will take much longer to heal (Leveen, H. et al., 1973). The bacteria present in an infection negatively affect the wound and its oxygen content. Bacteria and other factors can result in long periods of time in which the wound environment is at a basic pH. Because this can slow healing, measures are often taken to lower wound pH. Thus, measuring the pH of a wound can provide information about the stage of healing and the presence of infection.

Thus, there is a need for improved bandages capable of detecting pH to provide noninvasive, immediate information about a wound to help individualize treatment.

SUMMARY

At least in part, the present invention relates to a wound dressing, such as gauze, bandages, and surgical tapes, impregnated with a pH sensitive dye composition comprising an anthocyanin dye.

In some aspects, this disclosure provides a wound dressing. In some embodiments, the wound dressing comprising a substrate material and a pH sensitive dye composition disposed within the substrate material and comprising at least one fruit or vegetable derived anthocyanin.

As used herein, the terms "dressing" and "wound dressing" are used interchangeably and refer to a material applied to a wound to promote healing and/or prevent further harm.

As used herein, the term "wound" refers to an injury to living tissue caused by a cut, blow, laceration, surgical incision or other impact, typically one in which the skin is cut or broken. Types of injuries include, for example, cuts, scrapes, scratches, burns, blisters, insect bites, and surgical sites, to name a few.

In other aspects, this disclosure provides methods for manufacturing a wound dressing, comprising: providing a substrate material; and disposing pH sensitive dye composition comprising at least one fruit or vegetable derived anthocyanin within the substrate material.

Thus, the invention provides wound dressing and methods of use thereof, which utilize a pH sensitive dye composition comprising at least one fruit or vegetable derived anthocyanin. For example, a pH sensitive dye composition comprising at least one anthocyanin is derived from a fruit or vegetable selected from the group consisting of a red cabbage, purple cabbage, purple carrots, elderberry, hibiscus, purple potato, red currant, black currants, blueberries, cherries, purple grapes, red raspberries and black raspberries. In another exemplary embodiment, wound dressing and methods of use thereof that use a pH sensitive dye composition utilize a pH sensitive dye composition comprising at least one anthocyanin is derived from red cabbage. In another exemplary embodiment, wound dressing and methods of use thereof that use a pH sensitive dye composition utilize a pH sensitive dye composition comprising at least one anthocyanin is derived from a raspberry (*Rubus* sp.). In some embodiments, at least one anthocyanin is selected from the group consisting of cyaniding-3-sophoraside, cyanide-3-glucoside or pelargonidin-3-sophoroside.

Additionally, the "Anthocyanins" as used herein include anthocyanadin derivatives selected from the group consisting of cyandin, delphinidin, peonidin, petunidin, pelargonidin and malvidin anthocyanadin derivatives.

In some embodiments, the pH sensitive dye composition is sensitive at least within a pH range of pH 4.0 to pH 12.0, inclusive.

In some embodiments, the pH sensitive dye composition comprises a mordant, which are well known to the skilled artisan. For example, the pH sensitive dye composition may comprise a mordant selected from the group consisting of aluminum potassium sulfate, copper sulfate, iron (III) oxide, copper sulfate, citric acid, iron (III) sulfate ($Fe_2(SO_4)_3$) and sodium sulfate. In an exemplary embodiment, the mordant is aluminum potassium sulfate.

The wound dressing may be any dressing suitable for application to the surface of a wound, including, for example an open wound. In some embodiments, the wound dressing is selected from the group consisting of a pad, wrap, bandage, tape, cotton-tipped stick and adhesive strip bandage.

In some embodiments, the substrate material comprises an absorbent or water-permeable material. The absorbent or water-permeable material is capable of absorbing wound exudate. Suitable absorbent materials will preferably absorb at least about 10% by weight, at least about 20% by weight, at least about 30% by weight, at least about 50% by weight, at least about 75% by weight, or at least about 100% by weight of fluid or exudate. The dressing can be composed of a substrate material comprising woven materials, non-woven materials or both. In some embodiments, the dressing comprises a fabric, cloth or sponge material. The dressing may be composed of natural and synthetic materials. In an exemplary embodiment, the substrate material comprises cotton material including, cotton fabric or cotton gauze.

In some embodiments, the wound dressing further comprises at least one therapeutic agent selected from the group consisting of antimicrobial agents, antiseptic agents, anti-inflammatory agents, pain relieving agents, wound closing adhesive agents, and antihistamine agents.

The pH sensitive dye composition provides a clear and obvious indication of wound health. For example, the pH sensitive dye composition can provide an indication as to whether an antimicrobial therapy is effective for treating or preventing wound infection.

In some aspects, this disclosure provides methods for determining the status of a wound, the methods comprising applying a wound dressing on a wound surface, wherein the wound dressing comprises a substrate material, and a pH sensitive dye composition disposed within the substrate material and comprising at least one fruit or vegetable derived anthocyanin; and determining the status of the wound by assessing the color change of the pH sensitive dye composition after application of the dressing onto the wound surface.

In some other aspects, this disclosure provides methods treating a wound comprising: applying a wound dressing to the surface of the wound, wherein the wound dressing comprises a substrate material; and a pH sensitive dye composition disposed within the substrate material and comprising at least one fruit or vegetable derived anthocyanin; assessing the color of the wound dressing after application of the dressing onto the wound surface; and selecting a treatment plan based on the status of the wound based on the color of the wound dressing application to the wound surface.

In some embodiments, assessing the color change of the pH sensitive dye composition comprises monitoring the color change of the dressing over time. Assessing the color change of the pH sensitive dye composition may comprise monitoring the color change of the dressing for a period between 1 to 24 hours, a period of between 2 to 16 hours, a period of between 3 to 12 hours, a period of between 4 to 10 hours, or a period of between 6 to 8 hours after application of the dressing onto the wound surface. Assessing the color change of the pH sensitive dye composition may comprise monitoring the color change of the wound dressing at predetermined time intervals, such as, for example, one hour, two hour, four hour, six hour, eight hour, twelve hour or twenty-four hour time intervals following application of the dressing onto the wound surface.

The color change of the pH sensitive dye composition may be accomplished using the human eye or with the assistance of a visualization aide. For instance, assessing the color change of the pH sensitive dye composition can be performed by visual inspection or by using a color-sensing device. In some embodiments, the color-sensing device is selected from the group consisting of a colorimeter and a spectrometer.

Assessing the color change of the pH sensitive dye composition can be performed using an imaging device. In some embodiments, the imaging device is selected from the group consisting of a colorimeter, spectrometer, a digital camera, a mobile phone, a smartphone, a tablet, a portable computer, a computer, and a scanner.

In some embodiments, the methods provided herein further comprising removing or replacing the wound dressing when the color of the wound dressing indicates a basic pH.

In some aspects, the methods for treating a wound provided herein comprise selecting a treatment plan based on the status of the wound. The treatment plan can comprise removing or replacing the wound dressing when the color or the wound dressing indicates a basic pH. In some embodiments, the treatment plan comprises selectively administering one or more therapeutic agents and at least one therapeutic agent selected from the group consisting of antimicrobial agents, antiseptic agents, anti-inflammatory agents, pain relieving agents, wound closing adhesive agents, and antihistamine agents to the wound.

As used herein, the term "one or more" includes at least one, more suitably, one, two, three, four, five, ten, twenty, fifty, one-hundred, five-hundred, etc., of the item to which "one or more" refers. The term "at least one" as used in the present invention stands for one, two, three, four, five, ten, twenty, fifty, one-hundred, five-hundred, etc., or more of the item "at least one" refers to.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Figure 1:
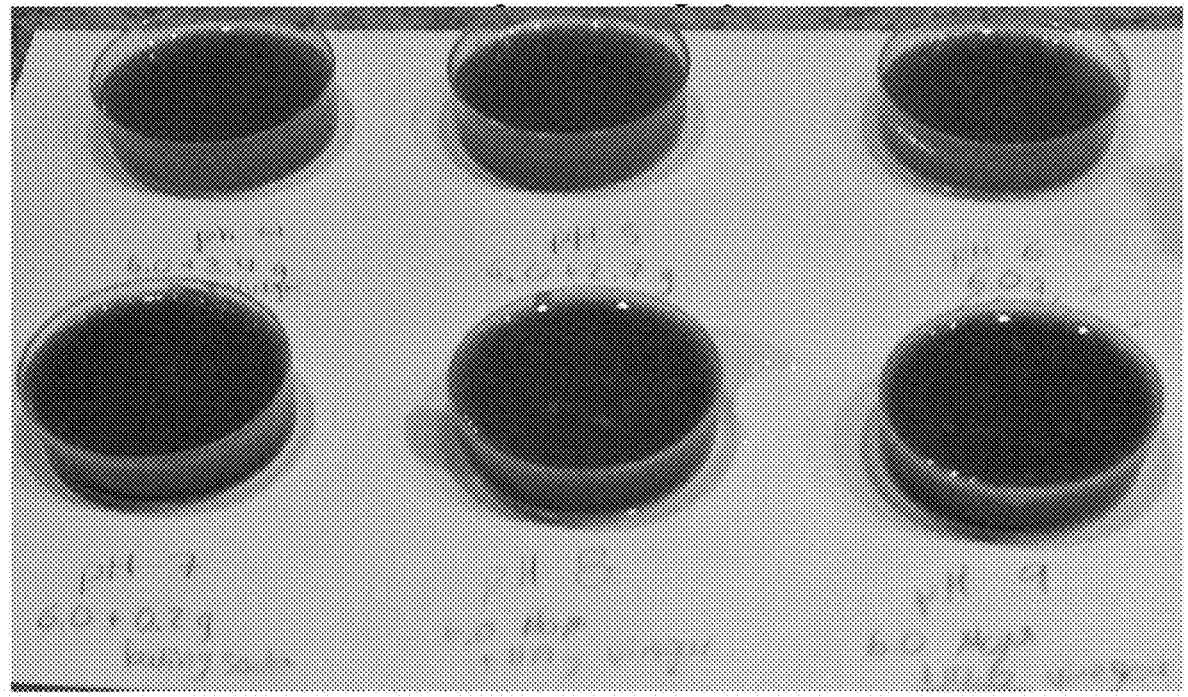
FIG. 1 is a photograph demonstrating the gradient of colors for raspberry puree at pH 4.0, pH 5.0, pH 6.0, pH 7.0, pH 8.0, and pH 9.0 (top row, left to right: pH 4.0, pH 5.0, pH 6.0; bottom row, left to right: pH 7.0, pH 8.0, pH 9.0).

Each line represents a pH, connecting the initial Red-Blue point to the final Red-Blue point, noted in black.

DETAILED DESCRIPTION

The present invention is based, in part, on the discovery that wound dressing materials impregnated with a pH-sensitive dye composition comprising at least one anthocyanin derived from a fruit or vegetable source, including for example an anthocyanin derived from raspberries (Rubus sp.), can be used on patients with long-term or chronic wounds to detect wound health and infection. Thus, in one aspect, the disclosure provides wound dressings designed for application to a wound, the wound dressing comprising a substrate material, and a pH sensitive dye composition disposed within the substrate material and comprising at least one anthocyanin dye derived from a fruit or vegetable. Advantageously, the wound dressings described herein absorb wound exudate and provide an indication of wound pH, and thus indication of wound health. The dressings provided herein provide noninvasive, immediate information about a wound to help individualize treatment.

In one aspect, the disclosure further provides methods for determining the pH of a wound, comprising contacting the wound with a dressing containing at least one anthocyanin dye derived from a fruit or vegetable; and monitoring the color change of the dressing material to determine the pH of the wound.

Wound dressings are often integral to wound healing. Wound dressings are prepared in many forms and for many different uses. Generally, a dressing is designed to be in direct contact with the wound and may be used in the form of a wrap or bandage. Aside from the major function of reducing the risk of infection, wound dressings are also important for providing a protective barrier from outside sources of irritation and provide mechanical support to the fragile wound surface. Wound dressings also function to absorb wound byproducts (e.g. excess blood, plasma, or other fluids) that tend to accumulate and complicate healing. Would dressings serve to form an occlusive barrier to provide an optimal environment for certain wound types, and act as an agent for wound debridement, which acts to clean and prepare a wound bed for healing.

The pH of a wound may be assessed using a wound dressing as disclosed herein, which changes color in dependence upon pH. Such wound pH information may be used to facilitate selection of the appropriate treatment to which the wound should be subjected. The wound dressing can be sterilized in an autoclave and loaded with antibacterial/antiseptic agents to provide a wound dressing which will indicate the pH of wound exudates in a non-invasive and simple manner.

In practice, a wound dressing as disclosed herein would be applied to a wound site of a subject with a surface of the wound dressing in contact with a surface of the wound. The wound dressing then would be monitored over a predetermined time period to assess the extent of the exudate present in the dressing.

Anthocyanins

In chemistry, chromism is a process that induces a reversible change in the colors of compounds. In most cases, chromism is based on a change in the electron states of molecules, so this phenomenon is induced by various external stimuli which can alter the electron density of substances. It is known that there are many natural compounds that have chromism, and many artificial compounds with specific chromism have been synthesized to date. Chromism is classified by what kinds of stimuli are used.

Color change can occur by changes in electromagnetic radiation, reflection, absorption or scattering. Thus, for example, photochromism signifies color change triggered by electromagnetic radiation; thermochromism signifies color change triggered by changes in temperature; electrochromism signifies changes in color occurring due to gain or loss of electrons; solvatochromism signifies color change resulting from changes in solvent polarity; ionochromism signifies color change caused by ions; tribochromism caused by changes in mechanical friction; piezochromism signifies changes caused by mechanical pressure; and halochromism signifies color change caused by a change in pH. Although fundamentally the halochromism is pH-dependent, the temperature-dependence of the acid-base equilibrium means that pH sensitivity can result in thermochromic behavior.

Anthocyanins are a class of halochromatic substances which respond to the level of acidity in an environment with a color change (Van der Schueren, L. & De Clerck, K., 2012). Anthocyanins pigments are responsible for the red, purple, and blue colors of many fruits and vegetables, including red and purple cabbage, beets, purple carrots, elderberry, hibiscus, purple potato, red and black currants, blueberries, cherries, purple grapes, and red and black raspberries. Within the plant they serve as key antioxidants and pigments contributing to the coloration of flowers. Anthocyanin pigment has a color gradient from orange to blue in the visible light spectrum, following the range of possible pH values. In the ultraviolet spectrum, the colors range from browns and yellows to purples and blues.

The color the anthocyanin molecule displays can change in relation to its environment; it is behind the color transition of green to red leaves from summer to autumn. These pigments are formed inside the plant through a metabolic pathway utilizing phenylalanine. Inside a plant cell, anthocyanins are dissolved in the water of the central vacuole where they can reflect outside light and give the plant cell its color. Bright pigments such as anthocyanins are evolutionarily beneficial to plants because they attract potential pollinators and may play a role in protecting photosynthetic pigments from light induced stress (Glover & Martin, 2012).

The color an anthocyanin molecule reflects is dependent on hydroxylation of two carbon rings in its molecular structure. For this reason, the pigment changes color in relation to the pH of its environment. When dissolved in an acidic solution containing a lower concentration of hydroxide ions, the pigments display colors ranging from orange to red. These colors are present in nature in a variety of plants, including raspberries and most other red fruits and vegetables. At a neutral pH, anthocyanins can appear violet or colorless, but as the pH increases, the color transitions to blue. Thus, the color or anthocyanin pigments has a direct relationship with the environment and follows a scale transitioning from red to blue as pH increases.

Anthocyanidins are the basic structures of anthocyanins, with formula (I) where $R_1$ to $R_7$ are, independently, H, OH or OMe.

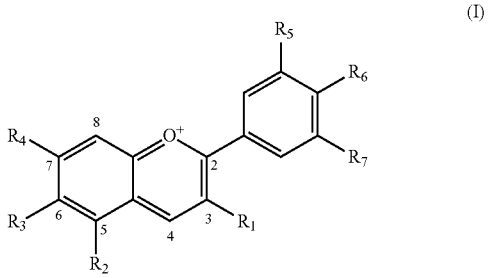

(I)

When anthocyanidins are found in their glycoside form (bonded to a sugar moiety) they are known as anthocyanins. There are reports of more than 500 different anthocyanins in nature. The main differences between them are the number of hydroxylated or methoxylated groups, the nature and number of sugars bonded to their structure, the aliphatic or aromatic carboxylates bonded to the sugar in the molecule and the position of these bonds. The substitution pattern of the six most common anthocyanidins and their abbreviations are shown in Table 1. The numbering of the substituents $R_n$ is as drawn in the formula (I) above.

TABLE 1

Common anthocyanidins

| Name (Abbreviation) | $R_1$ | $R_2$ | $R_3$ | $R_4$ | $R_5$ | R6 | $R_7$ |
|---|---|---|---|---|---|---|---|
| Cyanidin (CN) | OH | OH | H | OH | OH | OH | H |
| Delphinidin (Pp) | OH | OH | H | OH | OH | OH | OH |
| Pelagonidin (Pg) | OH | OH | H | OH | H | OH | H |
| Peonidin (Pn) | OH | OH | H | OH | OMe | OH | H |
| Petunidin (Pt) | OH | OH | H | OH | OMe | OH | OH |
| Malvidin (Mv) | OH | OH | H | OH | OmE | OH | OME |

In order of relative abundance, the sugars found bound to anthocyanidins to form anthocyanins are glucose, rhamnose, galactose, xylose, arabinose and glucuronic acid. The term "anthocyanin" as used herein is intended to include both glycosylated anthocyanins and acylated anthocyanins. The main glycoside derivatives in nature are 3-monosides, 3-biosides, 3,5-diglucosides and 3,7-diglucosides. Acylated anthocyanins derivatives include one or more molecules of the acyl acids; p-coumaric, ferulic and caffeic; or the aliphatic acids; malonic and acetic; and may be esterified to the sugar molecule. Overall, the most widespread anthocyanin is cyanidin-3-O-glucoside. The anthocyanins of the present invention may have the formula (I) wherein $R_1$, $R_2$ and $R_4$ are each independently H, OH, OMe, a sugar residue, or an acylated sugar residue; and $R_3$, $R_5$, $R_6$ and $R_7$ are each independently H, OH or OMe. The anthocyanins may be synthetic and/or natural anthocyanins.

In some embodiments, the at least one type of fruit or vegetable derived anthocyanin is obtained from a fruit or vegetable extract. By "obtained" or "obtaining" is meant purifying, extracting, synthesizing, purchasing, or otherwise acquiring an anthocyanin dye composition naturally found in raspberries.

An "extract" as used herein is a preparation made from any part or parts of a fruit or vegetable that comprises, generally in concentrated form, one or more anthocyanin compounds. The term "extract" is intended to include anthocyanin materials obtained from plant sources, such as leaves, roots, seeds, flowers, berries, fruit, for example, by routine isolation methods suitable from suitable plant sources. There are various methods for the extraction of anthocyanins known to those of skill in the art. The extract may be obtained from a fruit or vegetable selected from the group consisting of a red and purple cabbage, purple carrots, elderberry, hibiscus, purple potato, red and black currants, blueberries, cherries, purple grapes, and red and black raspberries.

The extract is typically concentrated by various methods to provide a solution enriched in anthocyanins. For example, ultrafiltration can be used to remove unwanted components by molecular weight cut offs. The retentate from the filtration can be stored as a liquid or, for example, can then be further concentrated into a powder by spray drying, freeze drying, flash drying, fluidized bed drying, ring drying, tray drying, vacuum drying, radio frequency drying or microwave drying. Ultimately, the extract should contain at least 10% by weight anthocyanin content. The extracts, therefore, contain anthocyanin(s) and may also contain other plant materials such as other flavinoids, sugars, etc.

In one embodiment, the disclosure provides a pH sensitive dye comprising at least one type of raspberry (Rupus sp.) anthocyanin (e.g., an anthocyanin extracted from a raspberry (Rupus sp.)). Raspberries belong to the genus Rubus. Cultivated raspberries have been derived mainly from two species, the wild red raspberry (Rubus ideaus) and black raspberry (Rubus occidentalis). Purple type is a cross between the black and red raspberry, and yellow type is a mutant red raspberry. There are over 200 species of raspberries. Raspberries can be grown from the Arctic to the equator. Anthocyanins obtained from raspberries (Rubus sp.) include, for example, an anthocyanin selected from the group consisting of cyanidin-3-sophoraside, cyanide-3-glucoside or pelargonidin-3-sophoroside.

In some embodiments, the anthocyanin is sensitive at least within a pH range of pH 6.0 to pH 8.0, a pH range of pH 5.0 to pH 9.0, a pH range of pH 4.0 to pH 10.0, a pH range of pH 2.0 to pH 13.0, or a pH range of pH 1.0 to pH 14.0. In one embodiment, the pH sensitive dye composition is sensitive at least within a pH range of pH 5.0 to pH 10.0.

In some aspects, the disclosure provides a pH sensitive dye composition comprising at least one type of anthocyanin derived from a fruit or vegetable. For example, the anthocyanin can be derived from red and purple cabbage, purple carrots, red and black currants, blackberries, blueberries, cherries, purple grapes, or red and black raspberries. In some embodiments, at least one type of anthocyanin is an anthocyanadin derivative selected from the group consisting of cyandin, delphinidin, peonidin, petunidin, pelargonidin and malvidin anthocyanadin derivatives. In some embodiments, the at least one type of anthocyanin is obtained from a raspberry (Rubus sp.) extract. In yet another embodiment, the at least one type of anthocyanin is obtained from a red cabbage extract.

The color change anthocyanin undergoes is not permanent, but will continue to respond to different stimuli as the environment changes. Thus, anthocyanins have reversible properties that make them reusable. This property makes anthocyanin useful as a pH indicator of solutions and substances, including washable and reusable dressings.

The pH sensitive dye composition changes color in response to changes in pH and provides an indicator of wound health. In some embodiments the pH sensitive dye composition is sensitive at least within a pH range of pH 6.0 to pH 8.0, a pH range of pH 5.0 to pH 9.0, a pH range of pH 4.0 to pH 10.0, a pH range of pH 4.0 to pH 12.0, a pH range of pH 2.0 to pH 13.0, or a pH range of pH 1.0 to pH 14.0.

In one embodiment, the pH sensitive dye composition is sensitive at least within a pH range of pH 5.0 to pH 10.0.

Dressing/Substrate Materials

The pH sensitive dye composition of the present invention may be used to color a variety of substrate materials. According to an aspect of the present invention, the pH sensitive dye composition is disposed within the substrate material of a wound dressing. More particularly, the pH sensitive dye composition is disposed within (e.g., impregnated within) said substrate material and trapped with the matrix of the substrate material. In some embodiments, the pH sensitive dye is dispersed homogenously (i.e., uniformly dispersed) throughout the dressing.

Conventional dressings include, for example, absorbent pads, absorbent cotton, gauze (e.g., gauze bandages and/or gauze pads), wrap (e.g., elastic wraps and/or gauze wraps), dermal patches, surgical drapes, bandage, tapes, cotton-tipped stick, adhesive bandages, or other support wrap or medical bandage or wound cover. The term "dressing" as used herein is also intended to cover casts (e.g., orthopedic cast, body cast, plaster cast, or surgical cast), frequently made from plaster, encasing a limb (or, in some cases, large portions of the body) to stabilize and hold anatomical structures, most often a broken bone (or bones), in place until healing is confirmed. In some embodiments, the dressing is a sterile dressing. The dressing may be disposable, washable and/or reusable.

In some embodiments, the dressing is an adhesive bandage. An adhesive bandage is usually covered by a woven fabric, plastic, or latex strip which has an adhesive. Adhesive bandages usually have an absorbent pad, which is sometimes medicated with an antiseptic solution. Some bandages have a thin, porous-polymer coating over the pad to keep it from sticking to the wound. The bandage is applied such that the pad covers the wound, and the fabric or plastic sticks to the surrounding skin to hold the dressing in place and prevent dirt from entering the wound. Adhesive bandages may include, but are not limited to, strip bandages, winged bandages, fingertip bandages, butterfly bandages, knuckle bandages, triangular bandages, tube bandages, compression bandages, elastic bandages, gauze bandages, donut bandages, pressure bandages, sterile-strips, eye bandages, sterile burn sheets, and adhesive tape.

In some embodiments, the substrate material comprises an absorbent or water-permeable material. The absorbent or water-permeable material is capable of absorbing wound exudate. The dressing can be composed of a substrate material comprising woven materials, non-woven materials or both. In some embodiments, the dressing comprises a fabric, cloth or sponge material. The dressing may be composed of natural and synthetic materials (e.g., natural or synthetic fibers). For example, the substrate material may be composed of natural or synthetic fibers selected from the group consisting of rayon, polyester, polyurethane, polyolefin, cellulose, cellulose derivatives, cotton, orlon, nylon, hydrogel polymeric material, and combinations thereof.

In use, the substrate material can be an elastic substrate. Materials suitable for use as an elastic substrate in the present invention include materials which are elastic, conformable, porous, provide adequate compression and which are self-adhering. In general, the material is sufficiently porous if the material allows for the transmission of air and moisture vapor through the material.

Mordants

In some aspects, the pH sensitive dye compositions disclosed herein further comprise a "mordant" or "mordanting agent." As used herein, the term "mordant" and "mordanting agent" are used interchangeably and refer to a substance capable of fixing and/or setting dyes on fabrics or tissue sections by forming a coordination complex with the dye, which then attaches to the fabric or tissue. A mordant may comprise metallic cations such as $Al^{3+}$ or $Fe^{3+}$ ions. In some embodiments, the mordant includes tannic acid, alum, chrome alum, sodium chloride, and certain salts of aluminum, chromium, copper, iron, iodine, potassium, sodium, and tin. Exemplary mordants for use in the dye compositions disclosed herein include, for example aluminum potassium sulfate, copper sulfate, iron (III) oxide, copper sulfate, citric acid, iron (III) sulfate ($Fe_2(SO_4)_3$) and sodium sulfate.

Therapeutic Agents

In some aspects, the wound dressings disclosed herein further comprise at least one therapeutic agent. For example, in addition to the pH sensitive dye compositions, the wound dressings of the present invention may further comprise at least one therapeutic agent disposed within the substrate material. Examples of therapeutic agents include, but are not limited to, antibiotic agents (e.g., antimicrobial agents and/or antiseptic agents), anti-inflammatory agents, pain-relieving agents, wound closing adhesive agents, or antihistamine agents.

In one embodiment, the wound dressings of the present invention advantageously comprise at least one antibiotic agent. For example, the wound dressings of the present invention may further comprise at least one antibiotic agent disposed within the substrate material. The antibiotic agent can be composed of any antibacterial compound that effectively prevents the growth of bacteria (e.g., bacteriostatic) or yeast (e.g. anti-yeast) and/or kills bacteria (e.g., bactericidal) or yeast once they are formed. The antimicrobial or antiseptic agents should preferably be safe, non-irritating, and hypoallergenic such that it does not cause any adverse reactions to the skin of the patient. Antibiotic agents that are suitable for use in the wound dressings include, for example, amikacin, amikacin sulfate, bacitracin, bacitracin zinc, chlortetracycline hydrochloride, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, oxytetracycline, paromomycin sulfate, polymyxin B, polymyxin B sulfate, sisomicin sulfate, sterile streptomycin sulfate, tetracycline hydrochloride, tobramycin and sterile tobramycin sulfate.

Methods for Assessing Wound Health

The treatment of body tissues, for example wounds to human or animal bodies can be problematic due to difficulties in assessing characteristics of the wound, for example the pH of exudates. To facilitate detailed assessment of a wound, correct diagnosis and hence selection of an appropriate treatment is needed.

In some aspects, the disclosure provides methods for determining the status of a wound by assessing the pH of a wound and/or wound exudate. Such wound pH information may be used to facilitate selection of the appropriate treatment to which the wound should be subjected.

In some embodiments, the methods for determining the status of a wound disclosed herein comprise applying a dressing on a wound surface, wherein the dressing comprises a substrate material, and a pH sensitive dye composition disposed within the substrate material comprising at least one type of fruit or vegetable derived anthocyanin; and determining the status of the wound by assessing the color change of the pH sensitive dye after application of the dressing onto the wound surface. The color change of the pH sensitive dye provides information about the pH of the wound, and thus provides information as to the status (e.g., health) of the wound.

In one embodiment, the pH of the wound is assessed on the basis of a change in the visual appearance of said substrate material. More specifically, the pH of the wound is assessed on the basis of the color of said substrate material. Assessing the color change of the pH sensitive dye composition comprises monitoring the color change of the dressing over time. Appropriate timing for monitoring the color change of the wound dressing may be determined by a healthcare professional or caregiver attending to the subject. For example, assessing the color change of the color of the pH sensitive dye composition may be performed by monitoring the color change of the dressing for a period between 1 to 24 hours, a period of between 2 to 16 hours, a period of between 3 to 12 hours, a period of between 4 to 10 hours, or a period of between 6 to 8 hours after application of the dressing onto the wound surface. In some embodiments, assessing the color change of the pH sensitive dye composition comprises monitoring the color change of the dressing at predetermined time intervals after application of the dressing onto the wound surface, i.e., at fifteen minute, thirty minute, one hour, two hour, four hour, six hour, eight hour, twelve hour or twenty hour time intervals after application of the dressing onto the wound surface.

The color change of the pH sensitive dye can be monitored by visual inspection (e.g., visual inspection by the human eye) or with the aid of a color-sensing device. Color sensing devices include, for example, a colorimeter or spectrophotometer. Colorimeters and spectrophotometers are well-known in the art and are used to measure certain optical properties of various materials. In addition to colorimeters and spectrometers, the color change of the pH sensitive dye can be monitored using an imaging device, such a digital camera, a mobile phone, a smartphone, a tablet, a portable computer, a computer, and a scanner.

Information on wound health aids healthcare professionals (e.g., a physician, physician assistant, pharmacist, nurse practitioner, nurse or case manager) and caregivers in determining the best treatment plan for a subject. In some embodiments, the method comprises assessing the color change of the pH sensitive dye after application of the dressing onto the wound surface; and, subsequently, carrying out another step in dependence upon the pH assessed. For example, the additional step can be advising a healthcare professional or caregiver to provide or select a treatment regimen for said wound, or advising a caregiver to remove/change/replace the wound dressing from the wound surface when the color of the wound dressing indicates a basic pH.

The pH sensitive composition may serve as an indicator of bacterial growth in the wound through the change in color thereof (the pH will stay basic). Following evidence of bacterial growth in the wound, the wound can be cleaned, disinfected, and dressed with a sterile dressing immediately after a wearer is aware of it.

The method may involve comparing the visual appearance, for example color, of the dressing with a reference means, for example a color reference means such as a color chart (or the like) to assess the pH of the dressing or environment.

The dressing material may be arranged to enable pH information to be obtained directly from it without recourse to any external reference means. For example, said test material may incorporate a said reference means suitably arranged to enable pH information to be obtained directly from the test material.

In some embodiments, the methods disclosed herein can include the step of recording information relating to the visual appearance (e.g., the color) of the substrate material. The color of the dressing may be recorded and/or the pH may be recorded. In yet another embodiment, the methods further comprise modifying the subject's clinical record to include information relating to the visual appearance (e.g., the color) of the wound dressing and the status of the wound. The clinical record may be stored in any suitable data storage medium (e.g., a computer readable medium).

EXAMPLES

The invention is further described in the following examples, which do not limit the scope of the invention described in the claims.

Experiments were conducted to evaluate the potential of anthocyanin in raspberries as a pH-sensitive dye. Raspberry juice (*Rubus* sp.) was mixed with an aluminum potassium sulfate mordant and processed, resulting in a dye that can be used to color cotton textiles. Cotton gauze bandages were dyed with this solution and wrapped around decomposing chicken, which had been treated with a range of pH values to simulate wound conditions. Changes in gauze color were observed by comparing RGB values before and after the bandages were exposed to the chicken. All bandages were sterilized in either an ethylene oxide machine or an autoclave before experimentation. The fabric was also detected *Staphylococcus aureus* in culture and could respond to pH changes more than once. The dye indicated pH and could safely be used on patients with long-term or chronic wounds to detect infection.

Description of Methods and Procedures:

A dye was made from raspberry juice and aluminum potassium sulfate. Cotton bandages were dyed and exposed to different pH levels as well as bacterial growth. Photographs were taken before and after the bandages were placed in different environments. The environments tested were pH values 5-9. Also, one group was exposed to bacterial growth on decomposing chicken. Red, green and blue values were extracted from the images using Adobe Photoshop Elements 11, and averaged to find before and after colors of each piece of cotton. The resulting color values were used to analyze the changes in color between each pH.

Testing for Halochromic Properties:

As an initial experiment, the inventor sought to test the halochromic properties of raspberry juice. Organic raspberries were pureed in a food processor until a thick, smooth mixture resulted. Petri dishes were prepared containing solutions varying in pH from 3 to 11 using baking soda, acetic acid (5% aqueous solution), and water. Each solution also contained a magnesium source which influenced pH; milk of magnesia ($Mg(OH)_2$) (CVS Brand, unflavored) was used in the basic solutions and magnesium citrate ($MgO_7C_6H_6$) (CVS Brand, lemon flavored) was used in the acidic petri dishes. When 6.0 grams of raspberry juice were added to the solutions they displayed a gradient of colors, shown in FIG. 1. Acidic pH solutions turned the raspberry puree redder, and a neutral environment changes the puree to a purplish color. Basic environments resulted in a drastic transformation to a blue-green color. The apparent color changes provided evidence that the main pigment (anthocyanin) is halochromic, which enabled the next test to be conducted.

Making a Raspberry Dye Preparation:

Raspberry juice does not fix naturally into cotton textiles, so two mordants were tested for their usefulness in attaching the juice to the fabric. Iron (III) oxide and aluminum potassium sulfate were selected as mordants. Each mordant was added to a solution consisting of equal parts water and raspberry puree and to a solution containing raspberry puree, water, and magnesium hydroxide (CVS Brand unflavored Milk of Magnesia).

Figure 2:
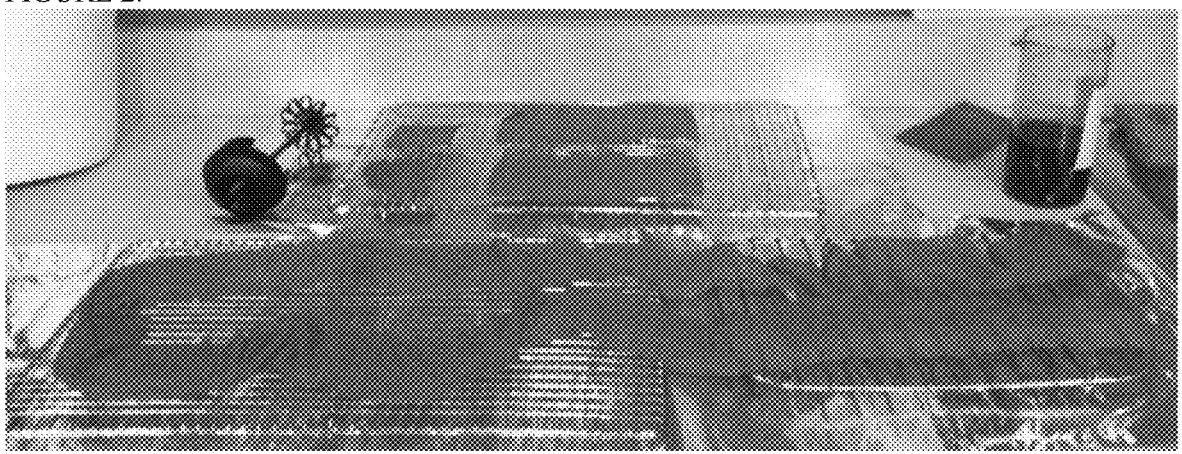
FIG. 2 is a photograph showing the bright red color of sample gauze and other medical bandages dyed with raspberry juice in an aluminum potassium sulfate solution without magnesium.

Dyeing Fabric:

Pieces of fabric were placed in each of the four prepared solutions, and the solutions were heated to 65° C. The aluminum mordant without the added magnesium worked best, producing a bright red color like that of raspberry fruit. (FIG. 2) The iron mordant without aluminum produced a duller, lighter red. Both pieces of fabric that were exposed to magnesium in solution did not dye evenly and resulted in spotted, uneven coloring. When exposed to different pH values, only the fabric dyed in an aluminum potassium sulfate solution without magnesium was capable of color change. This dye was selected as the optimum for dyeing fabric in future experiments.

Extracting Pigment:

In addition to dyeing fabric, attempts were made to extract a pigment from the dye for use in printing. The dye was concentrated by evaporating water and tested by writing with a quill. The aluminum potassium sulfate solution was tested with magnesium and without magnesium. The iron (III) oxide dye was not used in this testing due to the previous success of the aluminum potassium sulfate dye. The dyes were heated in test tubes in a beaker of water on a hot plate, and allowed to settle afterward. The solutions separated into different strata, but no solid pigment was available for extraction.

Both solutions were then used as pen ink. The magnesium containing solution did not adhere to paper and resulted in a light lavender, barely visible stain. The dark red solution without magnesium stained the paper where applied and turned a dark purple upon contact with the paper. It is presumed that this was due to the high pH of paper. The solutions were then tested against commercial calligraphy ink by exposing them to water and observing any running or fading. The calligraphy ink showed no change and the produced dye showed minimal fading. A solid pigment could not be extracted easily, and the dye was not concentrated enough to be used as professional ink, so dyeing fabric was pursued further. In addition, there are more potential uses for halochromic fabric than halochromic ink.

Example 1

Skin Simulation Experiment

Varying pH was shown to affect the dye, so an experiment was designed to test the color changes of the fabric in conditions mimicking the environment produced by a skin wound. Unflavored gelatin (Knox Brand) was set in petri dishes to replicate the surface of human skin, and holes were poked into the gelatin with a sewing needle to imitate pores that would leak bodily fluid. Each sample was then brushed with a solution of a different pH, varying from 5 to 9. The mixtures were allowed to briefly soak into each of the artificial pores, but some solution still remained on the surface of the gelatin. The pH solutions were produced with household items: lemon and lime juice were used to acidify pH values, water was used to neutralize pH values, and baking soda was used to alkalize pH values. A piece of sterilized gauze (CVS Brand) was then laid on the top of the gelatin in each petri dish. Four gauze samples were tested in each pH: two samples that had been previously soaked in acetic acid and two samples that had been previously rinsed in water. Before the samples were tested, they were sterilized in an ethylene oxide machine. The newly sterilized bandage squares were left on petri dishes of varying pH values for approximately 15 minutes to fully absorb the solution. After the allotted time, each piece was placed onto a white sheet of paper and photographed with a camera (Nikon D3100).

Color changes were observed and photographed, and numerical color values were extracted using Adobe Photoshop Elements 11. Each image was uploaded into the program and the brightness levels in the image were regulated. The color of the white paper surrounding the bandage in the photograph was set to be equal to absolute white in the image. This leveling process adjusted all of the colors accordingly, providing consistency between the colors in the images when they were all edited in this way. Next, each bandage was divided into squares and the Red-Green-Blue ("RGB") value of all of the pixels in each square was averaged. The RGB values of these squares were used for statistical testing.

Microbial Infection Simulation Experiment

Bacterial growth conditions were tested to determine if the dyed fabric could be used to signal bacterial infection by changing color when in contact with infected areas. First, 4 pieces of raw chicken (Purdue chicken breasts) were basted with solutions with pH 5 through pH 9. Then, strips of medical gauze dyed with the aluminum potassium sulfate dye were placed on pieces of chicken. The samples were each sealed in individual bags (Ziploc sandwich bags) and left in a residential garage for three days. The chicken was purposefully left to decompose to see what color changes the gauze would undergo in the presence of bacterial growth.

All 4 samples changed from their original color to the same shade of light blue when they were exposed to the microbial colonies. This color change began to occur during day 1 and day 2 of exposure to the chicken, as the bacteria began to grow. On the morning of the 3rd day, each gauze sample was photographed. The photographs were then uploaded to Adobe Photoshop Elements 11, where the RGB values of each pixel of the fabric were averaged and recorded. The resulting numbers were used in data analysis.

*Staphylococcus Aureus* Infection Simulation

The dyed fabric was exposed to *S. aureus* in petri dishes. The cultures were obtained from a laboratory at Becker College and remained in the laboratory and sealed for the duration of the observation. Before exposure to the bacteria, the bandages were dyed and rinsed in water to remove excess dye, resulting in a purple color. They were also autoclaved to before being exposed to the cultures to prevent outside contamination. The purple bandages were laid on top of *S. aureus* in petri dishes and observed after a two-day growth period. Photographs of the bandages were taken at this time to access color change. The bacterial colonies were autoclaved and discarded by a professional biohazard disposal company.

Results

Figure 3:
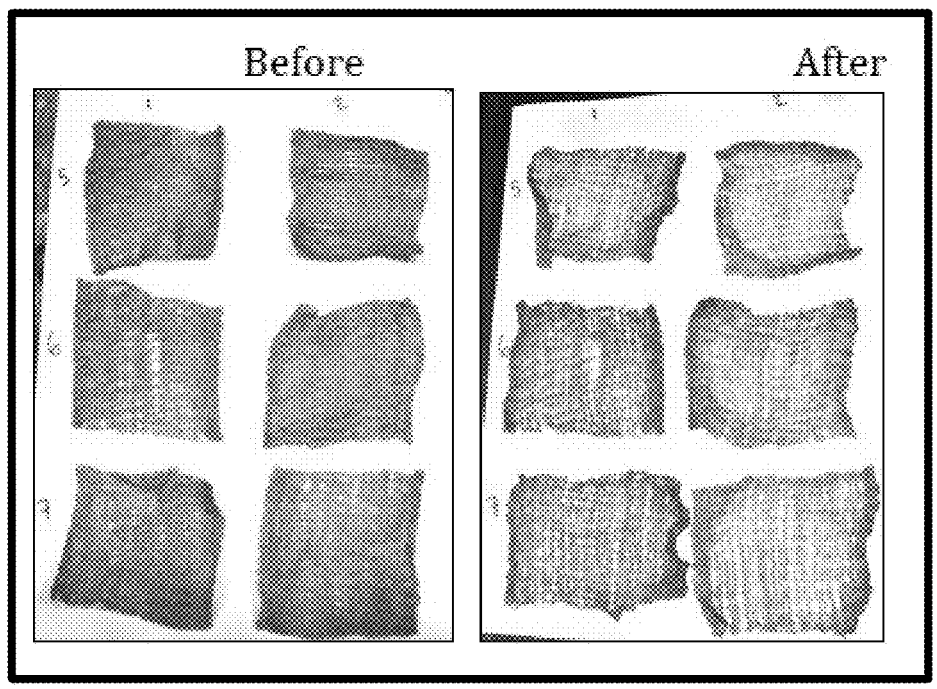
FIG. 3 are photographs demonstrating the color of dyed fabric before (left hand images) and after (right hand images) pH exposure (pH 5.0 (top row), pH 6.0 (middle row) and pH 7.0 (bottom row)).
Figure 4:
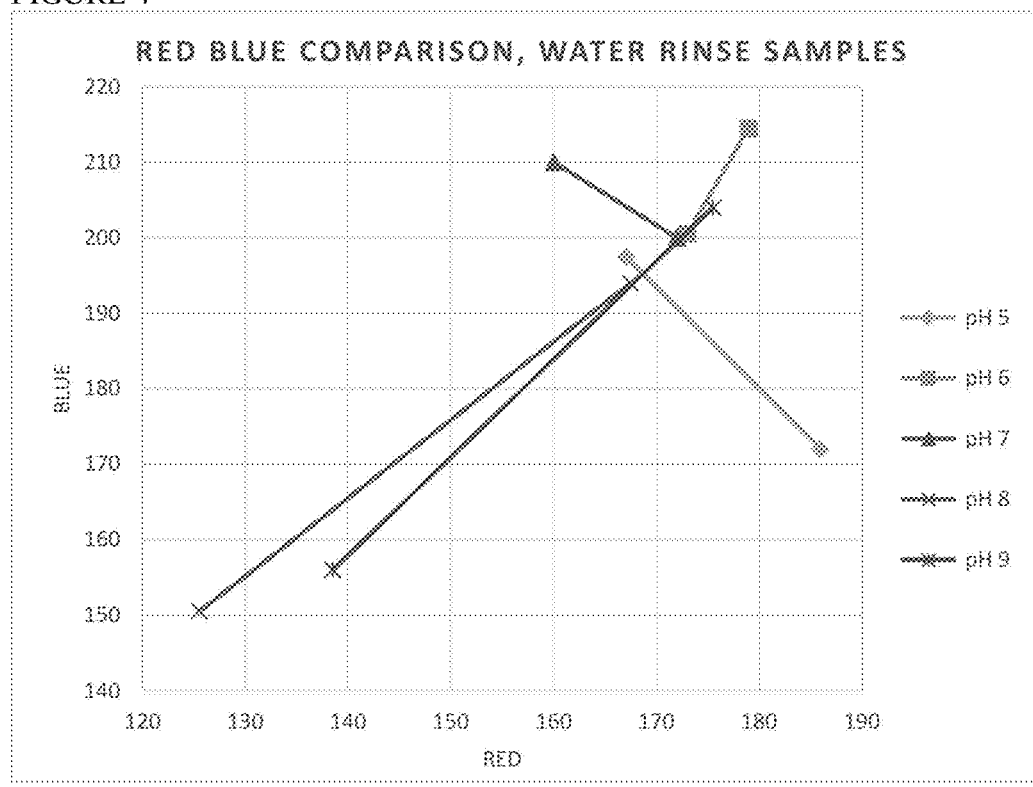
FIG. 4 is a graph demonstrating blue RGB values plotted against red RGB values before and after soaking. Each line represents a pH, connecting the initial Red-Blue point, noted in black, to the final Red-Blue point.

The data shows a clear relationship between pH and color. In the first test, the dyed fabric was rinsed with water to remove all extra dye. Specifically, two pieces of dyed, sterilized cotton bandage were washed in water and soaked in each pH 5 to 9 on top of gelatin to simulate skin conditions. Photos were taken before the pH was changed and afterward, and RGB values were obtained from these images and are recorded above. The photographs taken of the fabric after this process all show similar RGB values, shown by the low standard deviations (STDEV R=3.66, G=0.79, B=3.72) of each color value. When each square of fabric was exposed to the neutral pH of water, pH 7, the sections of bandage all displayed a similar color, which was violet. This color can be observed in FIG. 3, and in the RGB values in Table 1. FIG. 4 shows the blue RGB values obtained were plotted against the red RGB values before and after pH soaking. Each line represents a pH, connecting the initial Red-Blue point, noted in black, to the final Red-Blue point. In each fabric square, green is the lowest value and is not predominantly seen in the images. The blue value is the highest, followed by red, which combine to make the bluish purple seen in the fabric.

TABLE 1

| pH | Before R | Before G | Before B | After R | After G | After B |
|---|---|---|---|---|---|---|
| 5.0 | 167.0 | 151.5 | 197.5 | 186.0 | 136.5 | 172.0 |
| 6.0 | 173.0 | 152.0 | 200.5 | 179.0 | 147.0 | 214.5 |
| 7.0 | 172.0 | 152.5 | 200.0 | 160.0 | 165.5 | 210.0 |
| 8.0 | 167.5 | 151.0 | 194.0 | 125.5 | 127.0 | 150.5 |
| 9.0 | 175.5 | 153.0 | 204.0 | 138.5 | 138.5 | 156.0 |
| STDEV | 3.7 | 0.8 | 3.7 | 25.8 | 14.5 | 30.0 |

After this information was obtained, two bandage pieces were exposed to each of the pH values ranging from 5-9, inclusive. The photographs taken after this exposure show a much larger variance in color. Each RGB value was correlated to the pH, and there were large differences among them (STDEV R=25.81, G=14.50, B=29.99). Although each piece of fabric began at relatively the same color, different pH levels in each environment lead to varying colors. The color the fabric produced at each pH was also consistent. As seen by the similarities in the two sample groups (Appendix A), each pH caused a reliable color change. Exposing different cotton bandages dyed with the same dye to the same pH values used in this experiment would result in very similar RGB values. To ensure the results of this experiment were not by chance, an ANOVA test was run on the percent differences of both the red and blue values. An ANOVA was run on these values because they show that the Red-Blue color change, in comparison with the original values, was different in each environment. The test shows that this result is extremely unlikely to be achieved by random chance and that the data was statistically significant ($p=8.45*10^{-27}$).

Figure 5:
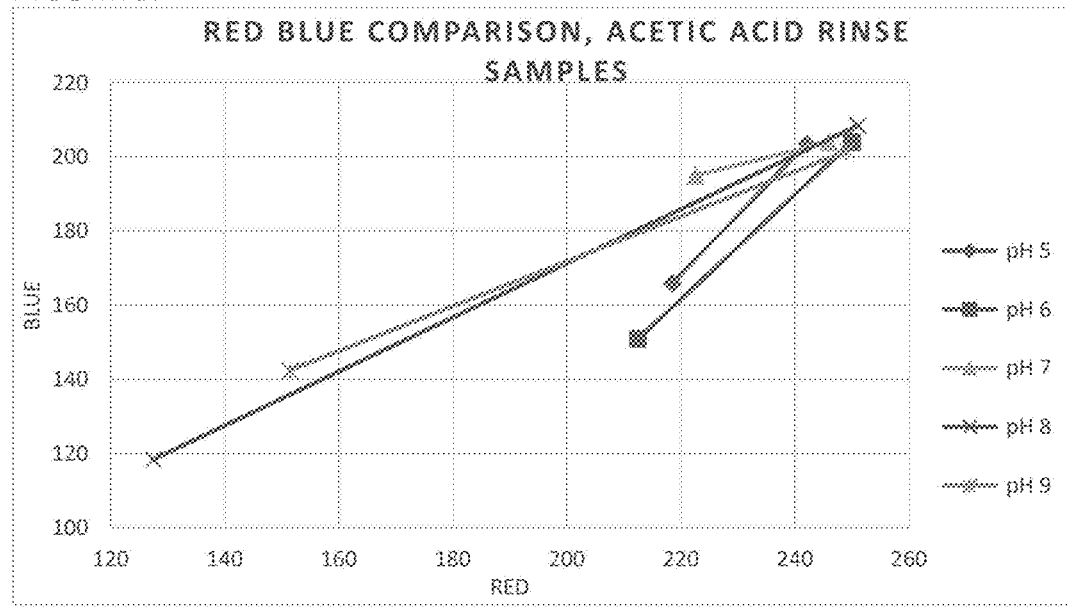
FIG. 5 is a graph demonstrating blue RGB values plotted against red RGB values before and after pH soaking. Each line represents a pH, connecting the initial Red-Blue point, noted in black, to the final Red-Blue point.

In the second experiment, the dyed fabric was rinsed with acetic acid before being exposed to varying pH values. Specifically, two pieces of dyed, sterilized cotton bandage were rinsed in acetic acid and then soaked in each pH 5 to 9 on top of gelatin to simulate skin conditions. Photos were taken before the pH was changed and afterward, and RGB values were obtained from these images and are recorded in the chart above. The acetic acid rinse was done to simulate the application of acetic acid to a wound, which is done to lower pH and promote healing. The starting RGB values for each separate bandage square obtained from images taken after the acetic acid rinse were very similar (STDEV R=3.65, G=1.85, B=2.56), showing that each bandage began at approximately the same color (Table 2, FIG. 5). This color was light pink, seen in the overall high RGB values that add brightness and the elevation of the Red value above the other two.

TABLE 2

| pH | Before R | Before G | Before B | After R | After G | After B |
|---|---|---|---|---|---|---|
| 5.0 | 242.0 | 189.0 | 203.5 | 218.5 | 161.0 | 166.0 |
| 6.0 | 250.0 | 191.0 | 204.0 | 212.5 | 151.5 | 151.0 |

TABLE 2-continued

| pH | Before R | Before G | Before B | After R | After G | After B |
|---|---|---|---|---|---|---|
| 7.0 | 246.0 | 194.0 | 204.0 | 222.5 | 200.0 | 195.0 |
| 8.0 | 251.0 | 191.5 | 208.5 | 127.5 | 125.5 | 118.5 |
| 9.0 | 249.0 | 192.5 | 201.5 | 151.5 | 147.5 | 142.5 |
| STDEV | 3.7 | 1.9 | 2.6 | 43.9 | 27.3 | 28.4 |

Despite starting at a very low pH (2 to 3), the fabric responded to environmental changes in pH and retained its halochromic properties. Two separate fabric sections were exposed to pH values 5 through 9 as in the previous test. The two samples in each environment were similar colors after testing (data not shown), showing the consistency of the color change. The colors resulting from the environments were very different (STDEV R=43.88, G=27.28, B=28.39) (Table 2). This shows that color changed drastically in the presence of unique pH values. To test if this result could be obtained by chance, an ANOVA was run on the distance between the percent differences of each color, as was done in the previous experiment. These numbers were chosen for the ANOVA because they represent the total Red-Blue color change for each pH compared with the original color. It can be said with confidence that the results show a color change that could not be achieved randomly and was statistically significant ($p=4.62*10^{-44}$). The bandages continued to respond to environmental pH changes even after they had been rinsed in acetic acid.

The color change after the acetic acid rinse followed the same gradient as the color change after the water rinse in the first experiment. Bandages in basic environments of pH 8-9 had lower RGB values overall resulting in a darker color and similar red and blue values, which give a blue-purple shade. Cotton pieces in neutral pH 7 had generally high RGB values, making them a lighter purple than the bandages in basic environments. The gauze in acidic environments of pH 5-6 displayed higher Red values compared to almost all of the other trials, giving them a more reddish hue than any of the other samples.

Figure 6:
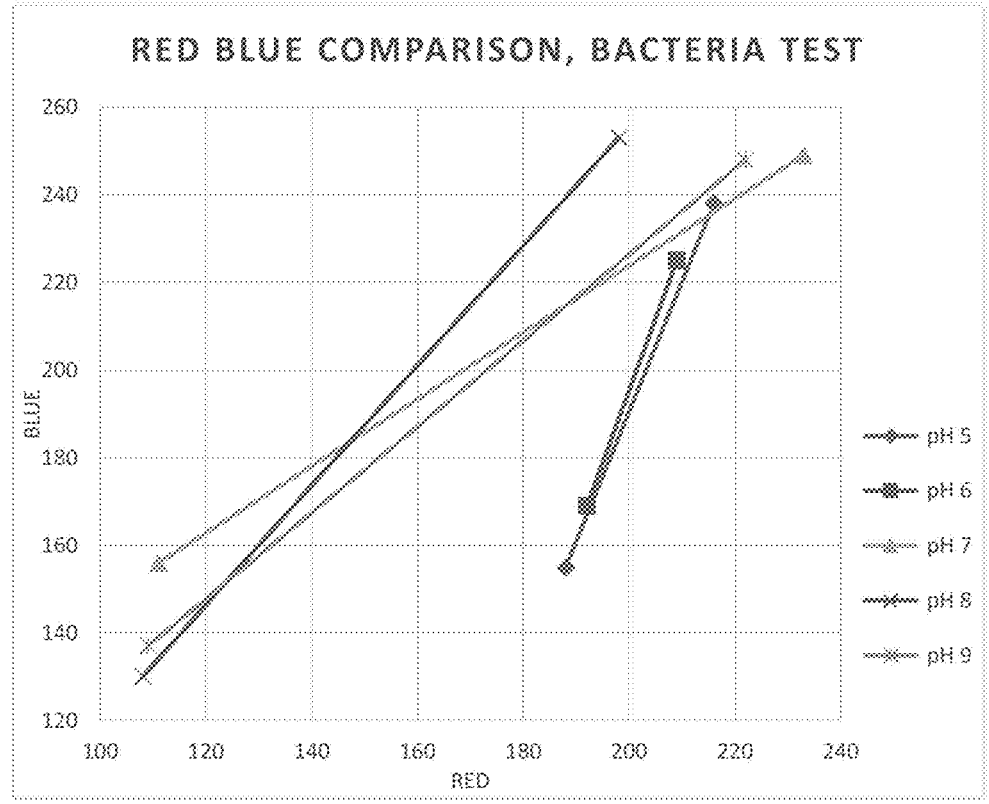
FIG. 6 is a graph demonstrating blue RGB values plotted against red RGB values before and after bacterial exposure.

The dyed gauze also showed a response to pH changes due to bacterial contamination. Cotton pieces were pre-soaked in each pH ranging from 5 to 9 and exposed to decomposing chicken. Before exposure to microbial populations, each square of fabric varied in RGB value (STDEV R=44.22, G=17.88, B=15.73), because each was a different color. After exposure to bacteria, the RGB values were much more similar between initial pH groups (STDEV R=13.20, G=10.49, B=11.28) (Table 3, FIG. 6). All of the Red, Green, and Blue values of the five samples increased, showing a consistently lighter color in the fabric when bacteria were present. Microbial contamination usually causes wound pH to become more basic, and the data collected also show this trend. The fabric squares in the previous experiment that were exposed to basic pH values exhibited a blue color, and the fabric in this experiment did the same. The Blue values are consistently higher than the Red values, showing that the basic environment produced by bacteria again resulted in a blue hue.

TABLE 3

| pH | Before R | Before G | Before B | After R | After G | After B |
|---|---|---|---|---|---|---|
| 5 | 188 | 141 | 155 | 216 | 241 | 238 |
| 6 | 192 | 158 | 169 | 209 | 220 | 225 |

TABLE 3-continued

| pH | Before R | Before G | Before B | After R | After G | After B |
|---|---|---|---|---|---|---|
| 7 | 111 | 122 | 156 | 233 | 243 | 249 |
| 8 | 108 | 116 | 130 | 198 | 247 | 253 |
| 9 | 109 | 119 | 137 | 222 | 239 | 248 |
| STDEV | 44.2 | 17.9 | 15.7 | 13.2 | 10.5 | 11.3 |

The fabric was also exposed to a specific type of bacteria, *Staphylococcus Aureus*. The fabric was sterilized in an autoclave before exposure to the bacteria to ensure no outside contamination would occur. The fabric began at a purple color after being rinsed in water, shown in Table 4.

TABLE 4

| Before Colors | | | After Color | | |
|---|---|---|---|---|---|
| R | G | B | R | G | B |
| 196 | 175 | 221 | 172.33 | 183.67 | 189.67 |
| 197 | 194 | 219 | | | |

Two shades of purple, which had high red and blue values, were used as starting colors: one from light rinsing in water with some excess dye still remaining and the other from a complete water rinse removing all unfixed dye. Both beginning colors turned into the same final color after the fabric was exposed to *S. aureus*. Three bandage samples were exposed to different *S. aureus* colonies in different petri dishes and the average RGB values were obtained from photographs of each sample. These values are in Table 4. This color change is significant because it shows that the fabric will indicate the presence of *S. aureus* with a color change to a bluish grey. The color change in the presence of this type of bacteria is consistent regardless of starting color, as shown by the starting color variations leading to the same final color. The fabric responded as was predicted because bacteria often create high pH environments, which would result in a bluish grey color similar to the final color of previous experiments. The dyed cotton gauze responded to changes in environmental pH in each test performed.

The data gathered in this experiment supported the hypothesis; the pH of an environment has an effect on the color of gauze dyed with a solution derived from raspberry juice. The color change follows a red to purple to blue gradient in accordance with pH as it changes from acidic to neutral to basic. The results of this project show that the raspberry dye made is halochromic and reusable, meaning it can react to changing pH more than once. Also, the dyed fabric can be easily sterilized using preexisting machinery, and it is still responsive to pH changes afterward. This includes environmental pH changes caused by bacteria, such as *S. aureus*, and other sources.

The experiments completed in this study provide strong evidence for the potential of halochromic gauze for use in the medical industry. Patients with long-term wounds such as lower extremity ulcers caused by diabetes could monitor their wounds at home with more certainty if they knew the pH of their wounds and the possible causes of pH changes. Color change was shown to be easily detectable in the fabric, and a layperson could observe the variations in color without outside assistance. This would provide more information about the health, stage of healing, and presence of infection in a wound to both the patient and the caretaker. The dyed gauze could also be used for patients who are advised to keep their bandages on for extended periods of time, such as a person wearing an Unna's boot. The fabric could also be used on patients with burns in order to learn more about the health of their wounds without removing the bandage, which is often a very painful process. In addition, the dyed gauze was sterilized successfully in both an autoclave and an ethylene oxide machine, showing it could be sterilized with existing equipment.

To be helpful to hospital patients with closely monitored wounds or people who are monitoring long-term wounds without professional assistance, the dyed cotton fabric used in this experiment could be made into smaller products for home use. This could help the layperson identify infection in small wounds and cuts. Overall, the cotton bandages in this experiment would be helpful in monitoring the state of any injury leaking bodily fluid.

LIST OF REFERENCES CITED

Gethin, G. (2007). The significance of surface pH in chronic wounds. Wounds uK, 3(3), 52.
Leveen H, et al., (1973) Chemical acidification of wounds. An adjuvant to healing and the unfavourable action of alkalinity and ammonia. Ann Surgery 178(6): 745-50.
Van der Schueren, L., & De Clerck, K. (2012). Coloration and application of ph-sensitive dyes on textile materials. Coloration Technology, 128, 82-90.
Glover, B. J., & Martin, C. (2012). Anthocyanins. Current Biology, 22(5), R147-R150.
Romanelli, M, et al., (2002) Technological Advances in Wound Bed Measurements, Wounds. 14(2).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the status of a wound, comprising:
    applying a wound dressing on a wound surface, wherein the wound dressing comprises a substrate material and a pH sensitive dye composition fixed to the substrate material by a mordant comprising aluminum potassium sulfate, wherein the pH sensitive dye composition comprises at least one fruit or vegetable derived anthocyanin, and the substrate material comprises a fabric, cloth or sponge material, and wherein color of the pH sensitive dye composition indicates pH of a wound; and
    determining the status of the wound by assessing the color change of the pH sensitive dye composition after application of the dressing onto the wound surface.

2. The method of claim 1, wherein the at least one anthocyanin is derived from a raspberry (*Rubus* sp.).

3. The method of claim 1, wherein the at least one anthocyanin is derived from a fruit or vegetable selected from the group consisting of a red cabbage, purple cabbage, purple carrots, elderberry, hibiscus, purple potato, red currant, black currants, blueberries, cherries, purple grapes, red raspberries and black raspberries.

4. The method of claim 1, wherein assessing the color change of the pH sensitive dye composition comprises monitoring the color change of the dressing over time.

5. The method of claim 1, wherein assessing the color change of the pH sensitive dye composition comprises monitoring the color change of the dressing for a period between 1 to 24 hours, a period of between 2 to 16 hours, a period of between 3 to 12 hours, a period of between 4 to 10 hours, or a period of between 6 to 8 hours after application of the dressing onto the wound surface.

6. The method of claim 1, wherein assessing the color change of the pH sensitive dye composition comprises monitoring the color change of the dressing at one hour, two hour, four hour, 6 hour, 8 hour, 12 hour or 24 hour time intervals after application of the dressing onto the wound surface.

7. The method of claim 1, wherein assessing the color change of the pH sensitive dye composition is performed by visual inspection.

8. The method of claim 1, wherein assessing the color change of the pH sensitive dye composition is performed using a color-sensing device.

9. The method of claim 8, wherein color-sensing device is selected from the group consisting of a colorimeter and a spectrometer.

10. The method of claim 1, wherein assessing the color change of the pH sensitive dye composition is performed using an imaging device.

11. The method of claim 10, wherein the imaging device is selected from the group consisting of a colorimeter, spectrometer, a digital camera, a mobile phone, a smartphone, a tablet, a portable computer, a computer, and a scanner.

12. The method of claim 1, further comprising removing or replacing the wound dressing when the color of the wound dressing indicates a basic pH.

13. A method of treating a wound comprising
applying a wound dressing to the surface of the wound, wherein the wound dressing comprises a substrate material and a pH sensitive dye composition fixed to the substrate material by a mordant comprising aluminum potassium sulfate, wherein the pH sensitive dye composition comprises at least one fruit or vegetable derived anthocyanin, and the substrate material comprises a fabric, cloth or sponge material, and wherein color of the pH sensitive dye composition indicates pH of a wound;
assessing the color of the wound dressing after application of the dressing onto the wound surface; and
selecting a treatment plan based on the status of the wound based on the color of the wound dressing applied to the wound surface.

14. The method of claim 13, wherein the treatment plan comprises removing or replacing the wound dressing when the color of the wound dressing indicates a basic pH.

15. The method of claim 13, wherein the treatment plan comprises selectively administering a one or more therapeutic agents least one therapeutic agent selected from the group consisting of antimicrobial agents, antiseptic agents, anti-inflammatory agents, pain relieving agents, wound closing adhesive agents, and antihistamine agents to the wound.

* * * * *